United States Patent
Ocampo

(10) Patent No.: US 10,444,094 B1
(45) Date of Patent: Oct. 15, 2019

(54) BLADDER SYSTEM FOR FORCE SENSITIVE RESISTORS (FSR) SENSORS

(71) Applicant: Flex Ltd., Singapore (SG)

(72) Inventor: Cesar Ocampo, Santa Clara, CA (US)

(73) Assignee: Flex Ltd., Singapore (SG)

( * ) Notice: Subject to any disclaimer, the term of this patent is extended or adjusted under 35 U.S.C. 154(b) by 0 days.

(21) Appl. No.: 16/035,447

(22) Filed: Jul. 13, 2018

Related U.S. Application Data

(60) Provisional application No. 62/532,799, filed on Jul. 14, 2017.

(51) Int. Cl.
G01L 1/22 (2006.01)
G01L 1/20 (2006.01)
A61B 5/00 (2006.01)

(52) U.S. Cl.
CPC .......... *G01L 1/2287* (2013.01); *G01L 1/205* (2013.01); *A61B 5/6807* (2013.01)

(58) Field of Classification Search
CPC .......... H01C 10/00; G01L 1/22; G01L 1/2287
See application file for complete search history.

(56) References Cited

U.S. PATENT DOCUMENTS

| | | | | |
|---|---|---|---|---|
| 3,830,991 A * | 8/1974 | Durocher | ............... | H01H 1/029 |
| | | | | 200/86 R |
| 4,017,697 A * | 4/1977 | Larson | ................. | H01H 13/702 |
| | | | | 200/5 A |
| 6,388,556 B1 * | 5/2002 | Imai | ......................... | G01L 1/20 |
| | | | | 338/114 |
| 6,483,055 B1 * | 11/2002 | Tanabe | ................... | H01H 3/141 |
| | | | | 200/512 |
| 7,112,755 B2 * | 9/2006 | Kitano | ...................... | G01L 1/20 |
| | | | | 200/17 R |
| 7,528,337 B2 * | 5/2009 | Tanabe | ...................... | G01L 1/20 |
| | | | | 200/511 |
| 2006/0131158 A1 * | 6/2006 | Takiguchi | ............ | H01H 13/702 |
| | | | | 200/512 |
| 2014/0015633 A1 * | 1/2014 | Nakae | .................. | H01H 13/785 |
| | | | | 338/47 |

* cited by examiner

*Primary Examiner* — Kyung S Lee
(74) *Attorney, Agent, or Firm* — Haverstock & Owens LLP

(57) ABSTRACT

A force sensing resistor (FSR) sensor with bladder system provides for ingress protection for FSR sensors by using sealed bladder areas, which act as air reservoirs. A sealed bladder area is attached to an air vent of a sensor area. The sensor area includes two conductive layers forming an open circuit in the static state, the two conductive layers separated by an air cavity. When a force is applied to the sensing area, the two conductive layers are forced toward each other to form a short circuit and the air in the air cavity is forced out the air vent into the bladder area. When the applied force is removed, the air in the bladder area returns into the air cavity separating the two conductive layers to form the open circuit. The bladder area provides a sealed environment within the FSR sensor, ensuring more reliable and consistent measurements.

25 Claims, 9 Drawing Sheets

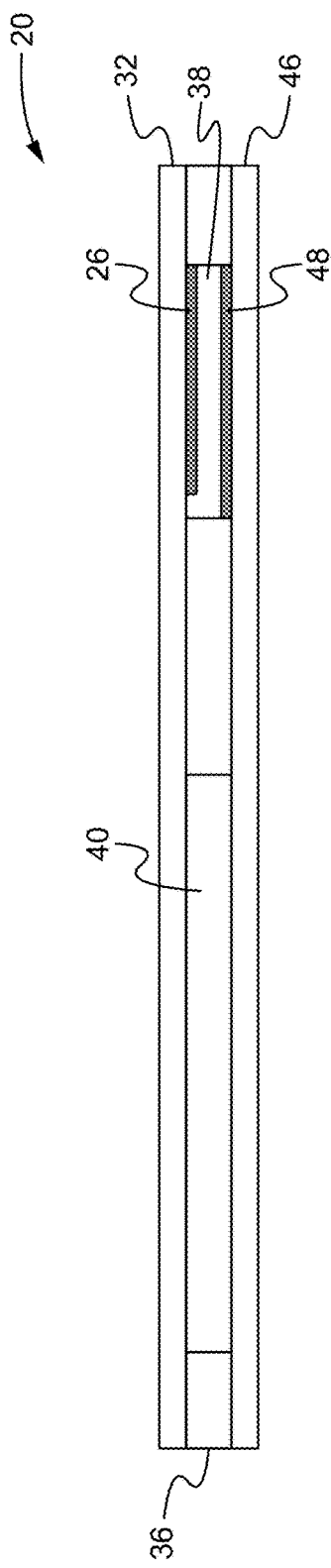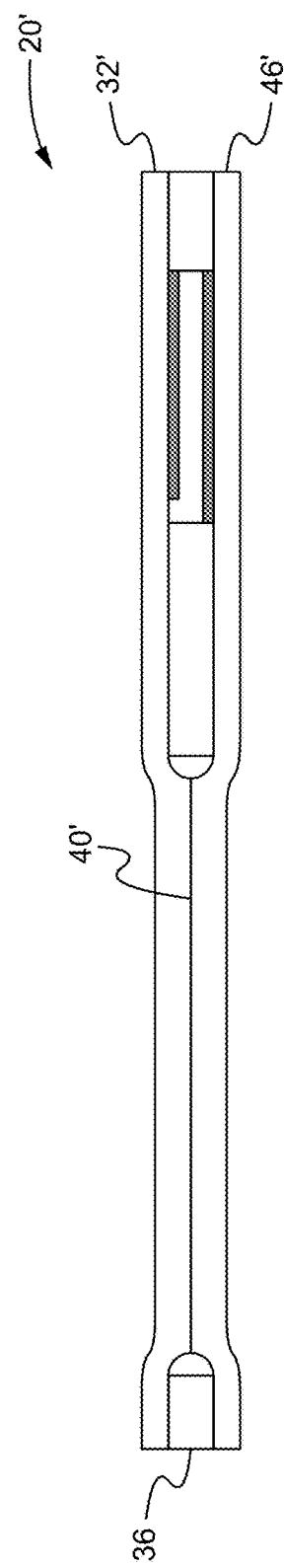

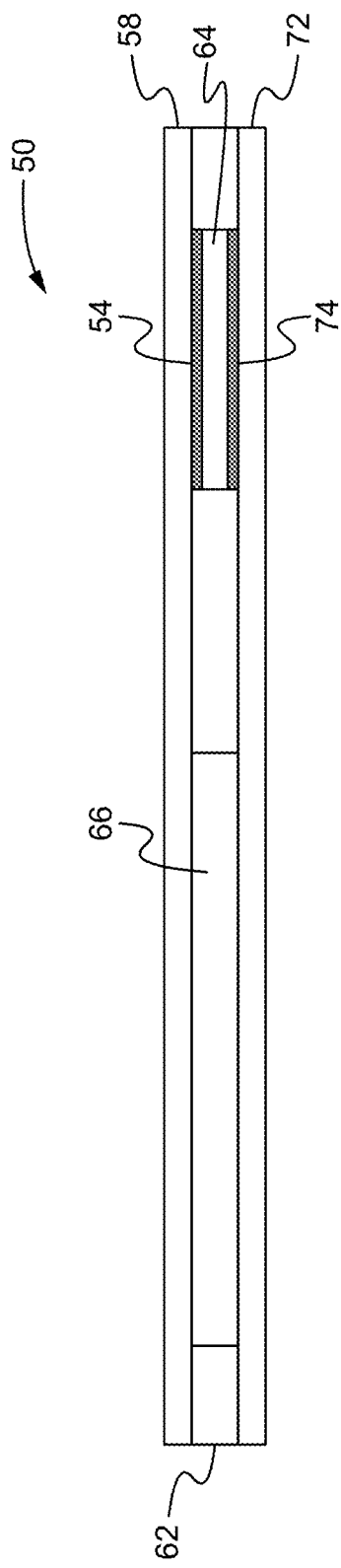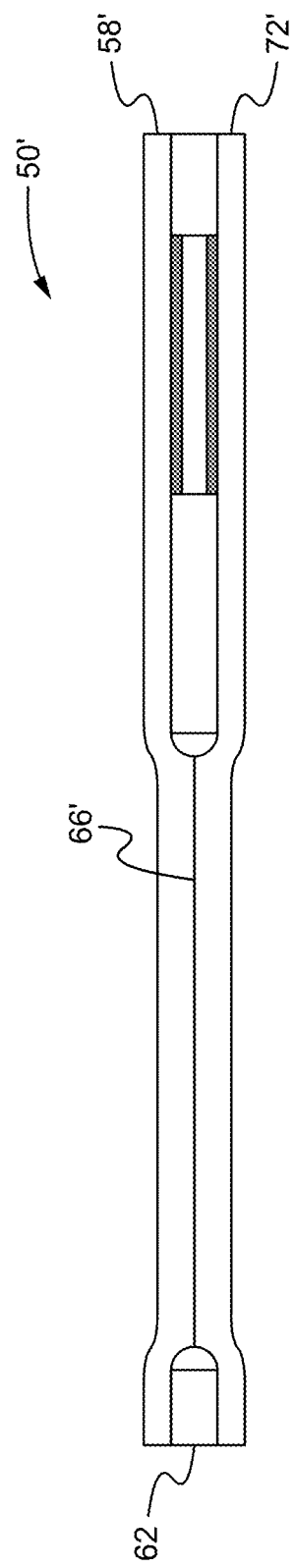

BLADDER SYSTEM FOR FORCE SENSITIVE RESISTORS (FSR) SENSORS

RELATED APPLICATIONS

This Patent Application claims priority under 35 U.S.C. 119(e) of the U.S. provisional patent application No. 62/532,799, filed on Jul. 14, 2017, and entitled "BLADDER SYSTEM FOR FORCE SENSITIVE RESISTORS (FSR) SENSORS," which is hereby incorporated by reference in its entirety.

FIELD OF THE INVENTION

The present invention is generally directed to force sensitive resistor (FSR) sensors. More specifically, the present invention is directed to a bladder system for FSR sensors.

BACKGROUND OF THE INVENTION

A force sensing resistor (FSR) sensor, also known as a FSR, a force sensor, or a pressure sensor, is a type of variable resistor whose resistance decreases when the applied force increases. If a large enough force is applied, a short circuit is formed enabling electric current flow. Additional force further decreases the resistance of the force sensitive resistor and provides corresponding lower resistance for the electric current. In contrast, if too small or no force is applied, the resistance remains and provides high resistance to the electric current. An amount of sensed current through the FSR sensor can be used to determine an amount of applied force. A typical FSR sensor includes a circuit having a first conductive layer, typically a conductive film, and a second conductive layer. In a static state, the first conductive layer and the second conductive layer are separated from each other by an air gap. This separation between the two conductive layers forms an open circuit, and no current flows through the circuit. When force is applied to one or both of the first and second conductive layers, the first and second conductive layers are forced toward each other. If sufficient force is applied, the first and second conductive layers contact each other causing a short circuit that enables current flow through the circuit. The circuit is sensed for current to determine a size of the force applied to the FSR sensor.

FIG. 1 illustrates an exploded view of a conventional FSR sensor. The conventional FSR sensor includes a first conductive layer 4 formed on a first substrate 2, a second conductive layer formed on a substrate 12, and a spacer 6 that separates the first conductive layer 4 and the second conductive layer. The second conductive layer is made of two patterned conductive traces 14 where the two patterned conductive traces are separated from each other to form an open circuit. Each patterned conductive trace 14 has a terminal extension 16 that provides an external connection to the FSR. The external connection is connected to a current source and a current sensing circuit. The spacer 6 includes an opening 8, which forms an air cavity between the first conductive layer 4 and the patterned conductive traces 14. The spacer 6 also includes an air vent 10 connected to the opening 8, which forms an air vent channel between the substrate 2 and the substrate 12 along the length of the terminal extensions 16. In an assembled, static state, the conductive layer 4 is separated from the patterned conductive traces 14 by the air gap in the opening 8. When a force is applied to either the substrate 2, the substrate 12, or both, the first conductive layer 4 and the conductive traces 14 are forced toward each other. If the applied force is great enough, some or all of the first conductive layer contacts some or all of the patterned conductive traces 14. In this contacted state, the first conductive layer 4 forms a shunt between the two separated patterned conductive traces 14, forming a short circuit. With the short circuit engaged, current flows from one of the patterned conductive traces 14 to the other, via the first conductive layer 4, and is sensed by the current sensing circuit indicating the presence of the applied force.

To enable the first conductive layer 6 and the patterned conductive traces 14 to move toward each other under applied force, the air in the cavity formed by the opening 8 must be vented out of the air vent 10. When the applied force is removed the first conductive layer 4 and the pattered conductive traces 14 move back to their static state positions, air returns into the cavity through the air vent 10. However, the air vented in and out of the air cavity in the opening 8 is vented to the environment, which allows dust and moister to enter into the FSR and in particular in between the first conductive layer 4 and the patterned conductive traces 14. Such contaminant ingress into the FSR may cause irregularities and interfere with the measurements.

SUMMARY OF THE INVENTION

The FSR sensor with bladder system provides for ingress protection for FSR sensors by using sealed bladder areas, which act as air reservoirs. In some embodiments, the bladder areas are pre-collapsed. A sealed bladder area is attached to an air vent of the FSR sensor. The FSR sensor includes two conductive layers forming an open circuit in a static state, the two conductive layers separated by an air cavity. When a force is applied to a sensing area, the two conductive layers are forced toward each other and the air in the air cavity is forced out the air vent into the bladder area. If sufficient force is applied, the two conductive layers are forced in contact with each other to form a short circuit. When the applied force is removed, the air in the bladder returns into the air cavity separating the two conductive layers to form the open circuit. Pre-existing air in the bladder increases the resistance to air flow out of the air cavity. In some applications, this air resistance is minimized by pre-collapsing the bladder area. The use of pre-collapsed bladder areas allows air to freely move from the air cavity under applied force, while maintaining a sealed environment. The pre-collapsed bladder area also forms a low pressure area allowing for air to move away from the air cavity and into the bladder area more easily. If the bladder area is not pre-collapsed, then pre-existing air within the non-collapsed bladder area resists air from the air cavity from flowing into the bladder area, which may inhibit sensor actuation and provide a false reading in some applications. Conventional FSR sensors vent out into the environment and enable dust and moisture to interfere with sensor measurements. Inclusion of a sealed bladder area provides a more controlled environment within the FSR sensor, ensuring more reliable and consistent measurements.

In an aspect, a force sensing resistor sensor is disclosed. The force sensing resistor sensor comprises a first layer, a second layer, and a middle layer. The first layer comprises a first flexible substrate and a first conductive layer coupled to the first flexible substrate. The second layer comprises a second flexible substrate and a second conductive layer coupled to the second flexible substrate, wherein the first conductive layer and the second conductive layer form part of an electric circuit. The middle layer comprises a middle substrate, a first opening through the middle substrate, and a second opening through the middle substrate, wherein the first opening is interconnected to the second opening. The first layer is stacked on the middle layer such that at least a portion of the first conductive layer is aligned over the first opening, and the middle layer is stacked on the second layer such that at least a portion of the second conductive layer is aligned over the first opening. The first layer covers the first opening and the second opening in the middle layer, and the second flexible substrate covers the first opening and the second opening such that the first opening forms an air cavity and the second opening forms a bladder area interconnected to the air cavity. The air cavity and the bladder area are a sealed environment. In some embodiments, the first layer is stacked on the middle layer such that the first conductive layer is facing the middle layer, and the middle layer is stacked on the second layer such that the second conductive layer is facing the middle layer. In some embodiments, the middle substrate further comprises an air channel, and the first opening is interconnected to the second opening through the air channel. In some embodiments, the portion of the first conductive layer aligned over the first opening, the first opening, and the portion of the second conductive layer aligned over the first opening form a sensor area. In some embodiments, the force sensing resistor sensor is configurable between a static state and an active state, wherein in the static state the portion of the first conductive layer in the sensor area is separated from the portion of the second conductive layer in the sensor area by air in the air cavity, further wherein in the active state at least one of the portion of the first conductive layer or the portion of the second conductive layer is forced into contact with the other of the first conductive layer or the portion of the second conductive layer. In some embodiments, forcing the portion of the first conductive layer and the portion of the second conductive layer into contact with each other forces air from the air cavity into the bladder area. In some embodiments, the force sensing resistor sensor is further configurable to return from the active state to the static state by removing the force applied to at least one of the portion of the first conductive layer or the portion of the second conductive layer, which separates the portion of the first conductive layer and the portion of the second conductive layer. In some embodiments, removing the force generates a vacuum in the air cavity that forces air from the bladder area back into the air cavity. In some embodiments, in the static state, the bladder area is filled with air. In some embodiments, in the static state the bladder is pre-collapsed. In some embodiments, in the static state the electric circuit is open circuited, and in the active state the electric circuit is closed circuited. In some embodiments, the first conductive layer and the second conductive layer are configured according to a shunt mode configuration. In some embodiments, the first conductive layer and the second conductive layer are configured according to a thru mode configuration.

In another aspect, a method of making a force sensing resistor sensor is disclosed. The method comprises forming a first layer that includes forming a first conductive layer on a first substrate, forming a second layer that includes forming a second conductive layer on a second substrate, and forming a middle layer that includes forming an air cavity and a bladder area within a third substrate, wherein the air cavity is coupled to the bladder area. The method further comprises stacking the first layer, the middle layer, and the second layer with at least a portion of the first conductive layer facing the middle layer and aligned with the air cavity, and at least a portion of the second conductive layer facing the middle layer and aligned with the air cavity. The portion of the first conductive layer, the portion of the second conductive layer, and the air cavity form a sensing area. The air cavity and the bladder area form a sealed environment within the force sensing resistor sensor. In some embodiments, forming the middle layer further comprises forming an air channel in the third substrate, wherein the air channel connects the air cavity to the bladder area. In some embodiments, the portion of the first conductive layer aligned over the first opening, the first opening, and the portion of the second conductive layer aligned over the first opening form a sensor area. In some embodiments, the force sensing resistor sensor is configurable between a static state and an active state, wherein in the static state the portion of the first conductive layer in the sensor area is separated from the portion of the second conductive layer in the sensor area by air in the air cavity, further wherein in the active state at least one of the portion of the first conductive layer or the portion of the second conductive layer is forced into contact with the other of the first conductive layer or the portion of the second conductive layer. In some embodiments, forcing the portion of the first conductive layer and the portion of the second conductive layer into contact with each other forces air from the air cavity into the bladder area. In some embodiments, the force sensing resistor sensor is further configurable to return from the active state to the static state by removing the force applied to at least one of the portion of the first conductive layer or the portion of the second conductive layer which separates the portion of the first conductive layer and the portion of the second conductive layer. In some embodiments, removing the force generates a vacuum in the air cavity that forces air from the bladder area back into the air cavity. In some embodiments, in the static state the bladder area is filled with air. In some embodiments, in the static state the bladder is pre-collapsed. In some embodiments, in the static state the electric circuit is open circuited, and in the active state the electric circuit is closed circuited. In some embodiments, the first conductive layer and the second conductive layer are formed according to a shunt mode configuration. In some embodiments, the first conductive layer and the second conductive layer are formed according to a thru mode configuration.

BRIEF DESCRIPTION OF THE DRAWINGS

Several example embodiments are described with reference to the drawings, wherein like components are provided with like reference numerals. The example embodiments are intended to illustrate, but not to limit, the invention. The drawings include the following figures:

FIG. 3 illustrates a cut out side view of the FSR sensor and bladder system of FIG. 2 in the static state along the line A-A'.

FIG. 4 illustrates a cut out side view of a FSR sensor and bladder system of FIG. 2 in the static state along the line A-A' that has a pre-collapsed bladder area.

FIG. 6 illustrates a cut out side view of the FSR sensor and bladder system of FIG. 5 in the static state along the line A-A'.

FIG. 7 illustrates a cut out side view of a FSR sensor and bladder system of FIG. 5 in the static state along the line A-A' that has a pre-collapsed bladder area.

DETAILED DESCRIPTION OF THE EMBODIMENTS

Embodiments of the present application are directed to a FSR sensor with bladder system. Those of ordinary skill in the art will realize that the following detailed description of the FSR sensor with bladder system is illustrative only and is not intended to be in any way limiting. Other embodiments of the FSR sensor with bladder system will readily suggest themselves to such skilled persons having the benefit of this disclosure.

Reference will now be made in detail to implementations of the FSR sensor with bladder system as illustrated in the accompanying drawings. The same reference indicators will be used throughout the drawings and the following detailed description to refer to the same or like parts. In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application and business related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

Figure 1:
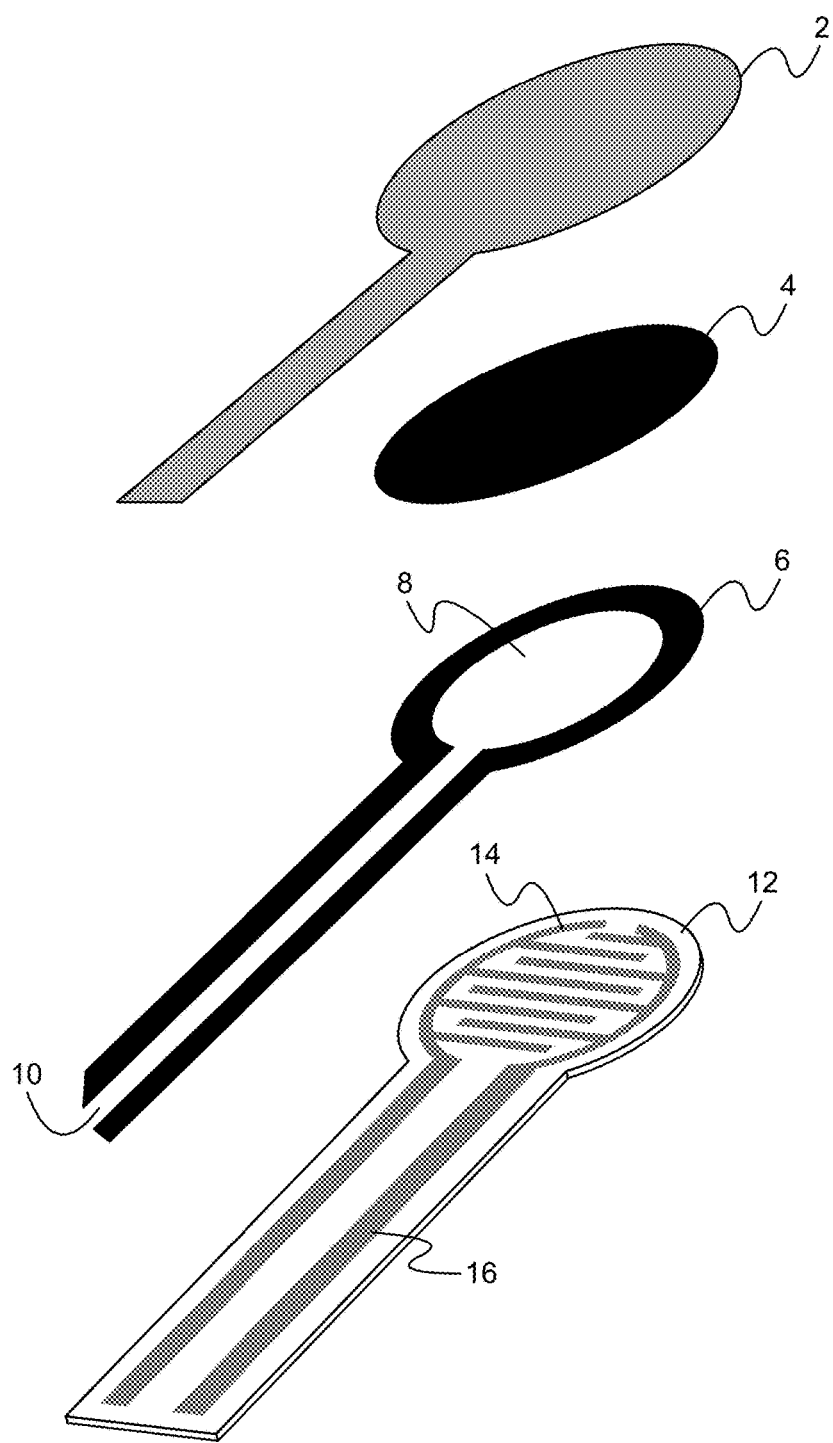
FIG. 1 illustrates an exploded view of a conventional FSR sensor.
Figure 2:
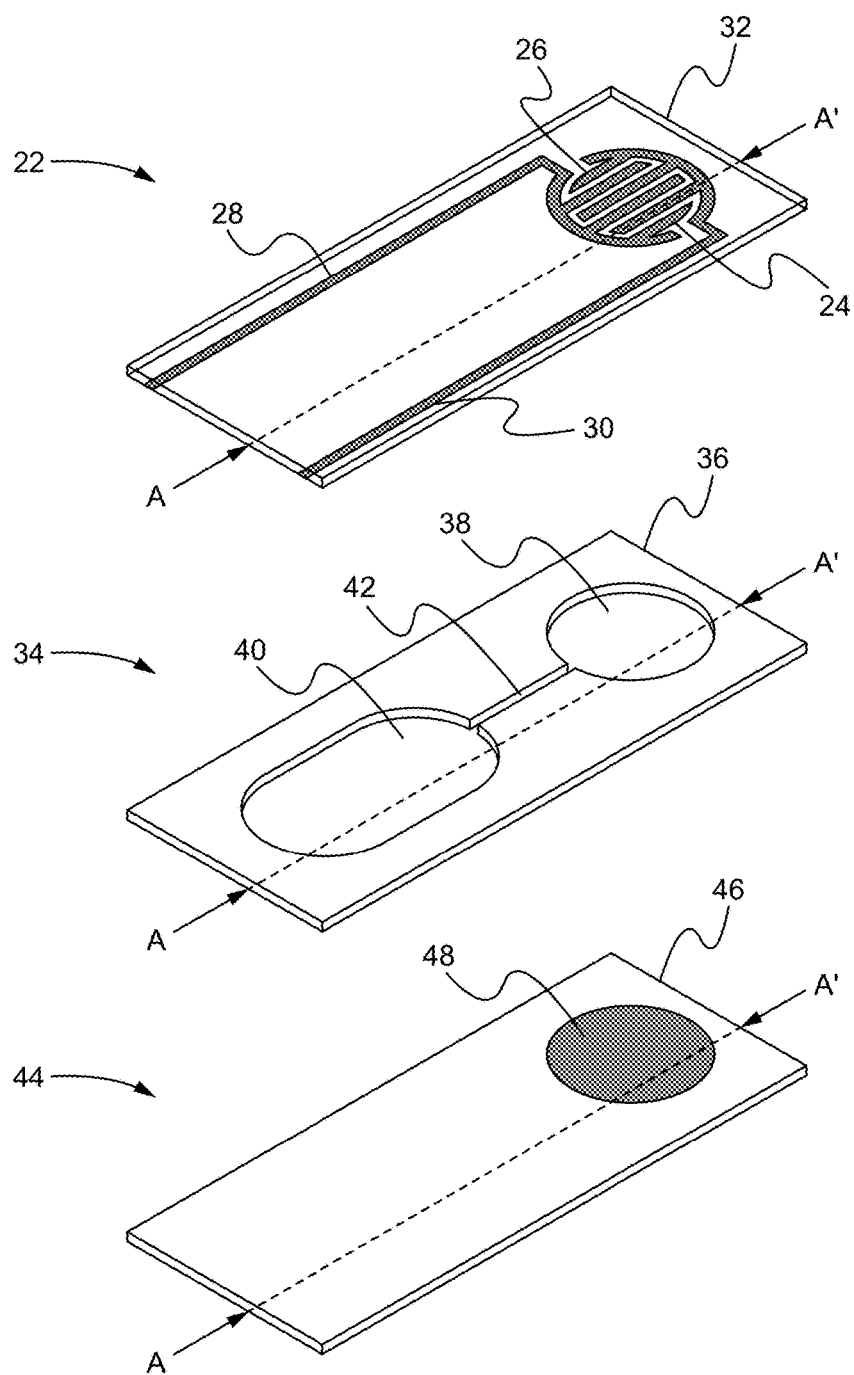
FIG. 2 illustrates an exploded view of an FSR sensor with bladder system according to some embodiments.

FIG. 2 illustrates an exploded view of an FSR sensor with bladder system according to some embodiments. The FSR sensor with bladder system 20 includes a first layer 22, a second layer 44, and a middle layer 34. The first layer 22 includes a substrate 32 with a conductive layer formed on a surface. The conductive layer is patterned and includes patterned conductive traces 24 and 26. The patterned conductive traces 24 and 26 are electrically isolated from each other and are therefore open circuited. It is understood that the patterned conductive traces 24 and 26 can be alternatively patterned from the patterns shown in FIG. 3. The patterned conductive traces 24 and 26 form conductive elements within a sensing area of the FSR sensor with bladder system 20. Conductive trace 28 is coupled to the patterned conductive trace 24, and conductive trace 30 is coupled to the patterned conductive trace 26. The conductive traces 28 and 30 extend away from the sensing area. Terminal ends of the conductive traces 28 and 30 are coupled to additional electronic circuitry (not shown) including, but not limited to, a current source and a current sensing circuit. The terminal ends of the conductive traces 28 and 30 can be coupled to connectors, such as staple connectors, or other conventional interconnection components for enabling connection to additional electronic circuitry that is off the FSR sensor and bladder system 20.

The substrate 32 is made of a flexible or semi-flexible, such as rigid-flexible, material that enables bending of the substrate, and in particular bending of the substrate in the sensing area, and corresponding patterned conductive traces 24, 26 under an applied force. Example substrate materials include, but are not limited to, polyimide, polyethylene terephthalate (PET), or other flexible, non-conductive materials. In some embodiments, the conductive traces 24, 26, 28, 30 are formed by laminating a conductive layer, such as copper, onto the substrate 32 and pattern etching the conductive layer. In other embodiments, conductive ink is printed, such as by screen printing, onto the substrate 32 to form the conductive traces 24, 26, 28, 30.

The second layer 44 includes a substrate 46 with a conductive layer 48 formed on a surface. The conductive layer 48 is formed in an area that substantially coincides with the sensing area of the FSR sensor and bladder system 20. In some embodiments, the conductive layer 48 is made of conductive polymer ink that is printed, such as screen printing, onto the substrate 46 to form the conductive layer 48. In other embodiments, the conductive layer 48 is formed by adhering a conductive polymer sheet to the substrate 46 and patterning the conductive polymer sheet. The substrate 46 is made of a flexible or semi-flexible material that can be the same, or different, than the material of substrate 32. The conductivity of the conductive polymer can be varied based on the selected materials. A less conductive polymer provides greater variability and improved ability to measure the applied force, as explained in greater detail below. In contrast, a greater conductive polymer provides less variability and reduced ability to measure the applied force.

The middle layer 34 includes a substrate that functions as a spacer between the first layer 22 and the second layer 44 to prevent the patterned conductive traces 24, 26 from contacting the conductive layer 46 while the FSR sensor with bladder system 20 is in a static state, where static state is the state when no external force is being applied to the sensing area. The substrate 36 can be rigid, flexible, or rigid-flexible. Example substrate materials include, but are not limited to, a pressure sensitive adhesive or a polymer. The substrate 36 includes openings 38 and 40 through the entire thickness of the substrate 36. The first layer 22, the middle layer 34, and the second layer 44 are stacked with the conductive traces 24, 26, 28, 30 of the first layer 22 facing the middle layer 34, and with the conductive layer 48 of the second layer 44 facing the middle layer 34. The first layer 22, the middle layer 34, and the second layer 44 are also stacked together such that the patterned conductive traces 24, 26, the opening 38, and the conductive layer 48 are co-aligned to form the sensing area. Additional adhesive, such as pressure sensitive adhesive or other type of adhesive, can be applied to the substrate 36 and/or the substrate 32 and/or the substrate 46 for stacking. The opening 38 forms an air cavity that separates the patterned conductive traces 24, 26 and the conductive layer 48, which prevents the patterned conductive traces 24, 26 and the conductive layer 48 from shorting while in the static state. The opening 40 forms a bladder area that is connected to the air cavity 38. In the exemplary embodiment shown in FIG. 2, the air cavity 38 is connected to the bladder area 40 by an air channel 42 formed in the substrate 36. Alternatively, the air cavity 38 is connected directly to the bladder area 40. The bladder area 40 and the air channel 42 are not considered part of the sensing area. The air cavity 38 and the bladder area 40, as well as the air channel 42, are formed by the substrate 32, the substrate 36 and the substrate 46, which forms a sealed environment that is isolated from the ambient environment outside the FSR sensor and bladder system 20.

In operation, electrical circuitry connected to the conductive traces 28, 30 monitors for a current. The amount of current sensed is used to determine a corresponding force applied at the sensing area. In the static state, the patterned conductive traces 24 and 26 are open circuited, and no current flows through the circuit, which corresponds to zero applied force measurement at the sensing area. Force can be applied at the sensing area to the substrate 32, to the substrate 46, or to both. In an exemplary case, force is applied to the substrate 32, which forces the patterned conductive traces 24, 26 toward the conductive layer 48. If sufficient force is applied, which corresponds to a threshold applied force, the patterned conductive traces 24, 26 and the conductive layer 48 contact each other, in which case the conductive layer 48 forms a shunt between the patterned conductive trace 24 and the patterned conductive trace 26, forming a closed circuit. The closed circuit enables current flow which is measured and used to determine a corresponding amount of applied force. As the applied force is increased beyond the threshold applied force, the resistance of the conductive layer 48 decreases, resulting in increased current flow. The variable resistivity of the conductive layer 48 is a function of the physical properties of the materials used to make the conductive layer 48, such as a conductive polymer. When the applied force is removed, or reduced below the threshold applied force, the substrate 32 springs back to its static state form, and the patterned conductive traces 24, 26 and the conductive layer 48 are again separated, forming the open circuit.

When the patterned conductive traces 24, 26 and conductive layer 48 are forced toward each other, air in the air cavity 38 is forced out and into the bladder area 40. When the applied force is removed, the elastic nature of the substrate 32 returns the substrate to its static state form creating a vacuum in the air cavity that draws back into the air cavity 38 from the bladder area 40. In this manner, air within the air cavity-bladder area system remains isolated.

In some embodiments, the first layer 22, the middle layer 34, and the second layer 44 are stacked such that air is present in both the air cavity, the air channel, and the bladder area when the FSR sensor and bladder system 20 is in the static state. FIG. 3 illustrates a cut out side view of the FSR sensor and bladder system 20 of FIG. 2 in the static state along the line A-A'. In this embodiment, both the air cavity 38 and the bladder area 40 are filled with air when the FSR sensor and bladder system 20 is in the static state.

With air is present in both the air cavity 38 and the bladder area 40 in the static state, the pre-existing air within the bladder area 40 provides some resistance to the air exiting the air cavity 38 when force is applied to the sensing area. This added resistance to air flow may impact the sensitivity of the sensor and resulting force measurements. In some applications, a greater degree of sensitivity may be desired. The added air resistance can be reduced, if not eliminated, by pre-collapsing the bladder area. FIG. 4 illustrates a cut out side view of a FSR sensor and bladder system of FIG. 2 in the static state along the line A-A' that has a pre-collapsed bladder area. The FSR sensor and bladder system 20' is similar to the FSR sensor and bladder system 20 of FIGS. 2 and 3, cut along the line A-A', but the bladder area 40' is pre-collapsed such that little, if any, air is present in the bladder area 40' while the FSR sensor and bladder system 20' is in the static state. In some embodiments, the bladder area 40' is pre-collapsed during the assembly process when the layers 22, 34 and 44 are stacked together. During the stacking step, additional pressure can be applied to either the substrate 32, the substrate 46, or both, at the area(s) coincident with the bladder area, thereby pushing the substrates 32, 36 toward each other and collapsing the bladder area. In the exemplary configuration shown in FIG. 4, both the substrate 32 and the substrate 46 are forced inward at the bladder area to form pre-collapsed bladder area 40'. Heat and pressure can be applied at this step to thermoform, or otherwise form, the substrate 32' and substrate 40' into the altered static state forms, as shown in FIG. 4, necessary for pre-collapsing the bladder area 40'. It is understood that the static state form can be alternatively formed. For example, only the substrate 32 can be pressed to form the pre-collapsed bladder, in which case the static state form of the substrate 46 in a pre-collapsed bladder embodiment is similar to the form of substrate 46 shown in FIG. 3. As another example, only the substrate 46 can be pressed to form the pre-collapsed bladder, in which case the static state form of the substrate 32 in a pre-collapsed bladder embodiment is similar to the form of substrate 32 shown in FIG. 3.

Figure 5:
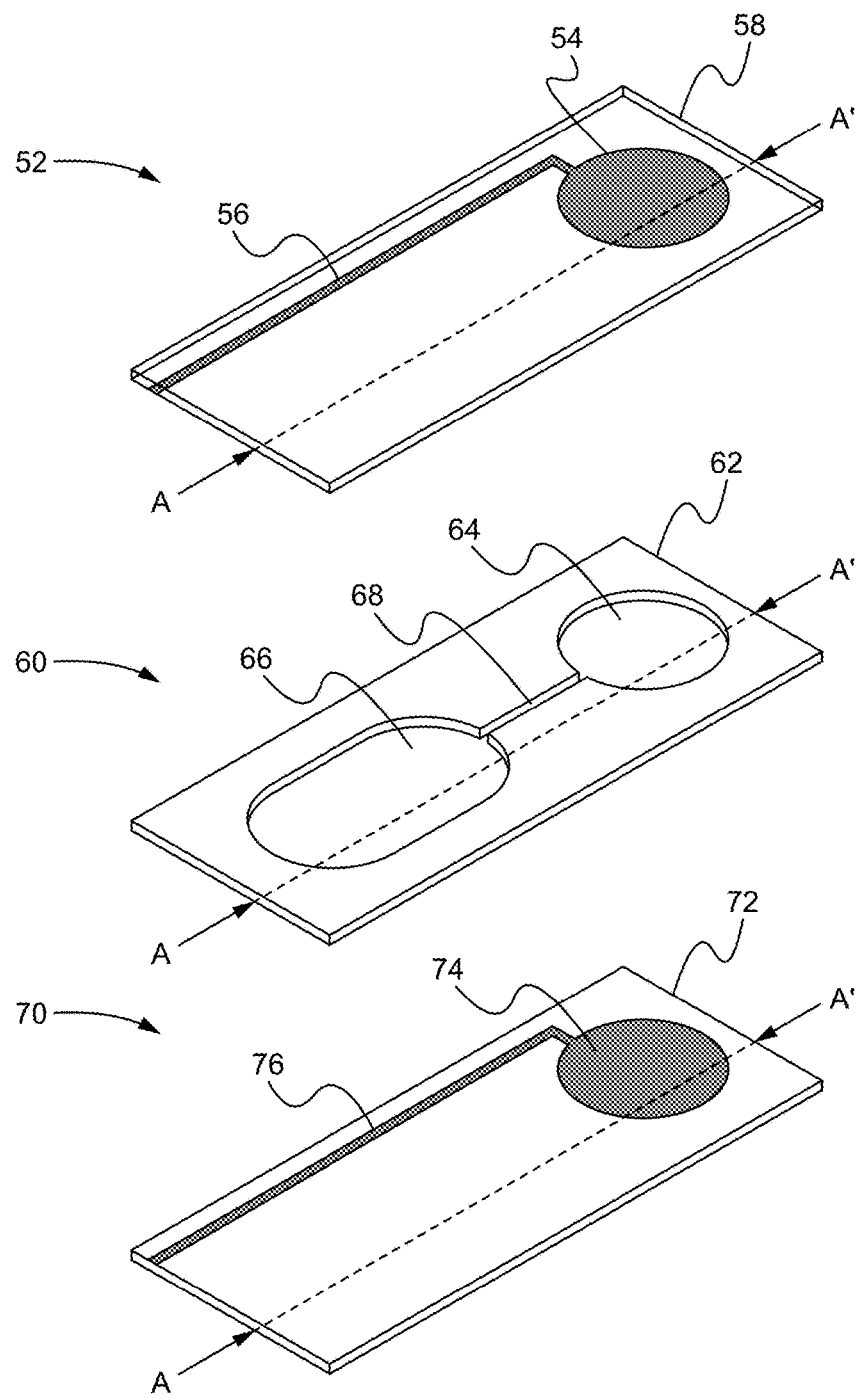
FIG. 5 illustrates an exploded view of an FSR sensor with bladder system according to other embodiments.

The exemplary embodiments shown and described in relation to FIGS. 2-4 above describe a shunt mode configuration. In the shunt mode configuration, current flows to and from the sensing area on the first layer, for example through the conductive traces 28 and 30. Alternatively, the FSR sensor and bladder system can be configured according to a thru mode where current flows to the sensing area on one of the first or second layers, but the current flows away from the sensing area on the other of the first or second layers. FIG. 5 illustrates an exploded view of an FSR sensor with bladder system according to other embodiments. The FSR sensor with bladder system 50 includes a first layer 52, a second layer 70, and a middle layer 60. The FSR sensor with bladder system 50 is similar in structure and function as the FSR sensor with bladder system 20 of FIG. 2 except the FSR sensor with bladder system 50 is configured according to a thru mode. In particular, the second layer 70 includes a substrate 72 with a conductive layer 74 formed on a surface. The conductive layer 74 is formed in an area that substantially coincides with the sensing area of the FSR sensor and bladder system 50. The second layer 70 additionally includes a conductive trace 76 coupled to the conductive layer 74. The conductive trace 76 can be made of the same conductive material as the conductive layer 74, for example a conductive polymer, or the conductive trace 76 can be made with a different conductive material, such as the conductive materials described above in relation to the patterned conductive traces 24, 26 and conductive traces 28, 30 of the FSR sensor and bladder system 20. Alternatively, conductive materials such as those described above in relation to the patterned conductive traces 24, 26 and conductive traces 28, 30 of the FSR sensor and bladder system 20 can be used to as a conductive layer applied to the substrate 72 in a pattern matching that of areas 74 and 76 shown in FIG. 5, and an additional conductive layer, for example the conductive polymer, can be applied over the conductive material in the area 74, for example by printing the conductive polymer onto the conductive material already applied in the area 74. In this case, the conductive layer within the sensing area formed on the substrate 72 can be considered a stack of two conductive layer materials. As used herein, reference to the conductive layer 74 can refer to either the single conductive layer configuration or the two conductive layers configuration. The first layer 52 can be similarly configured as the second layer 70 including a substrate 58 with a conductive layer 54 formed on a surface, and a conductive trace 56 coupled to the conductive layer 54. Similar to the second layer 70, the conductive areas 54, 56 can be configured similarly as the conductive areas 74, 76. The middle layer 60 can be similarly configured as the middle layer 34 of the FSR sensor and bladder system 20. In the exemplary embodiment shown in FIG. 5, the middle layer 60 includes an opening 64, an opening 66, and an air channel 68. It is understood that alternative configurations can be used to implement a thru mode configuration. For example, an additional layer can be stacked between the first layer 52 and the middle layer 60, and between the middle layer 60 and the second layer 70, where each additional layer includes a substrate, a conductive layer aligned with the sensing area, and a conductive trace connected to the conductive layer. In such an example the additional layers enable taking two measurements at the same sensing area location, and account for variations.

The first layer 52, the middle layer 60, and the second layer 70 are stacked in a manner previously described, where the conductive layer 54 and the conductive layer 74 are aligned with the opening 64 to form a sensing area having air cavity 64. The air cavity 64 and the bladder area 66 form a sealed environment. In some embodiments, the first layer 52, the middle layer 60, and the second layer 70 are stacked such that air is present in both the air cavity, the air channel, and the bladder area when the FSR sensor and bladder system 50 is in the static state, as shown in FIG. 6. The cut out side view shown in FIG. 6 corresponds to FSR sensor and bladder system 50 of FIG. 5 cut along line A-A'. In other embodiments, the FSR sensor and bladder system of FIG. 5 can be configured with a pre-collapsed bladder area 66', as shown in the cut out side view of FIG. 7.

The patterned conductive traces, such as the open circuited patterned conductive traces 24, 26, used in the shunt mode configuration provide an initial higher resistivity and increase the variability of the force reading as compared to the continuous conductive layers, such as the conductive layers 54 and 74, in the thru mode configuration because the resistance change with applied force is more gradual.

The FSR sensor and bladder system is described and shown above as including a single sensor area and a single bladder area connected to the single sensor area. The FSR sensor and bladder system can alternatively be configured to have multiple sensor areas, each sensor area connected a common bladder area. The FSR sensor and bladder system can also be configured with multiple sensor areas and multiple bladder areas, each bladder area connected to one or more of the sensor areas and/or each sensor area connected to one or more bladder areas. Bladder areas connected to more than one sensor area are increased in size to accommodate the potential input air flow from each of the connected sensor areas.

Figure 8:
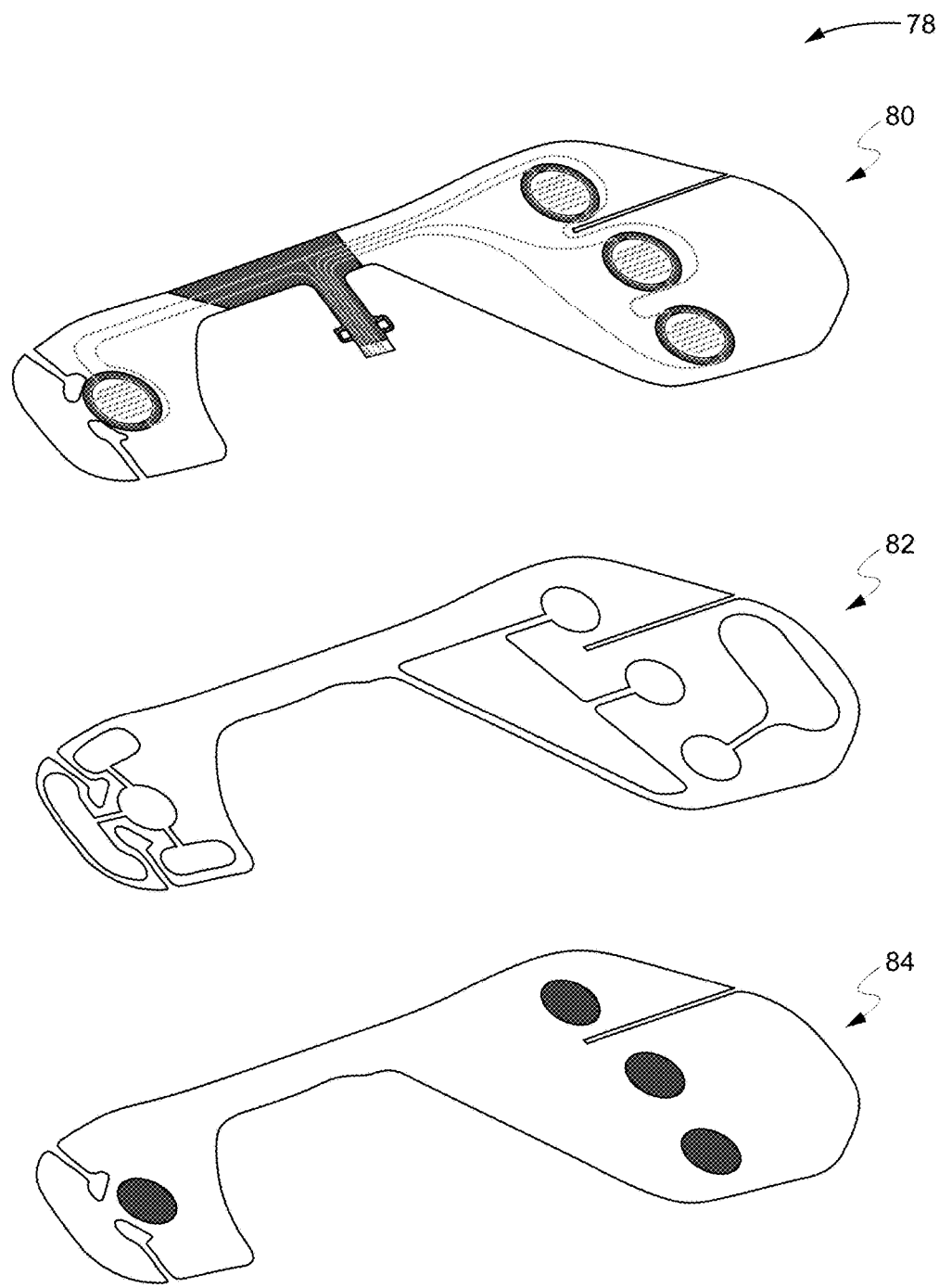
FIG. 8 illustrates an exploded view of a FSR sensor and bladder system implemented as part of a sole of a shoe according to some embodiments.

The FSR sensor and bladder system embodiments are described above as general use applications and can be used in applications that would benefit from a sealed sensor area and improved reliability. In an exemplary application, the FSR sensor and bladder system is configured as part of a force sensing system within the sole of a shoe or other form of footwear. An example of an applied external force in such an application is when a foot presses down on the FSR sensor and bladder system, such as when a person is walking and the shoe contacts the ground during a step. FIG. 8 illustrates an exploded view of a FSR sensor and bladder system implemented as part of a sole of a shoe according to some embodiments. The FSR sensor and bladder system 78 includes a first layer 80, a middle layer 82, and a second layer 84. The FSR sensor and bladder system 78 and constituent layers can be structured and operated in a manner conceptually similar as the FSR sensor and bladder systems 20 and 20' of FIGS. 2-4.

Figure 9:
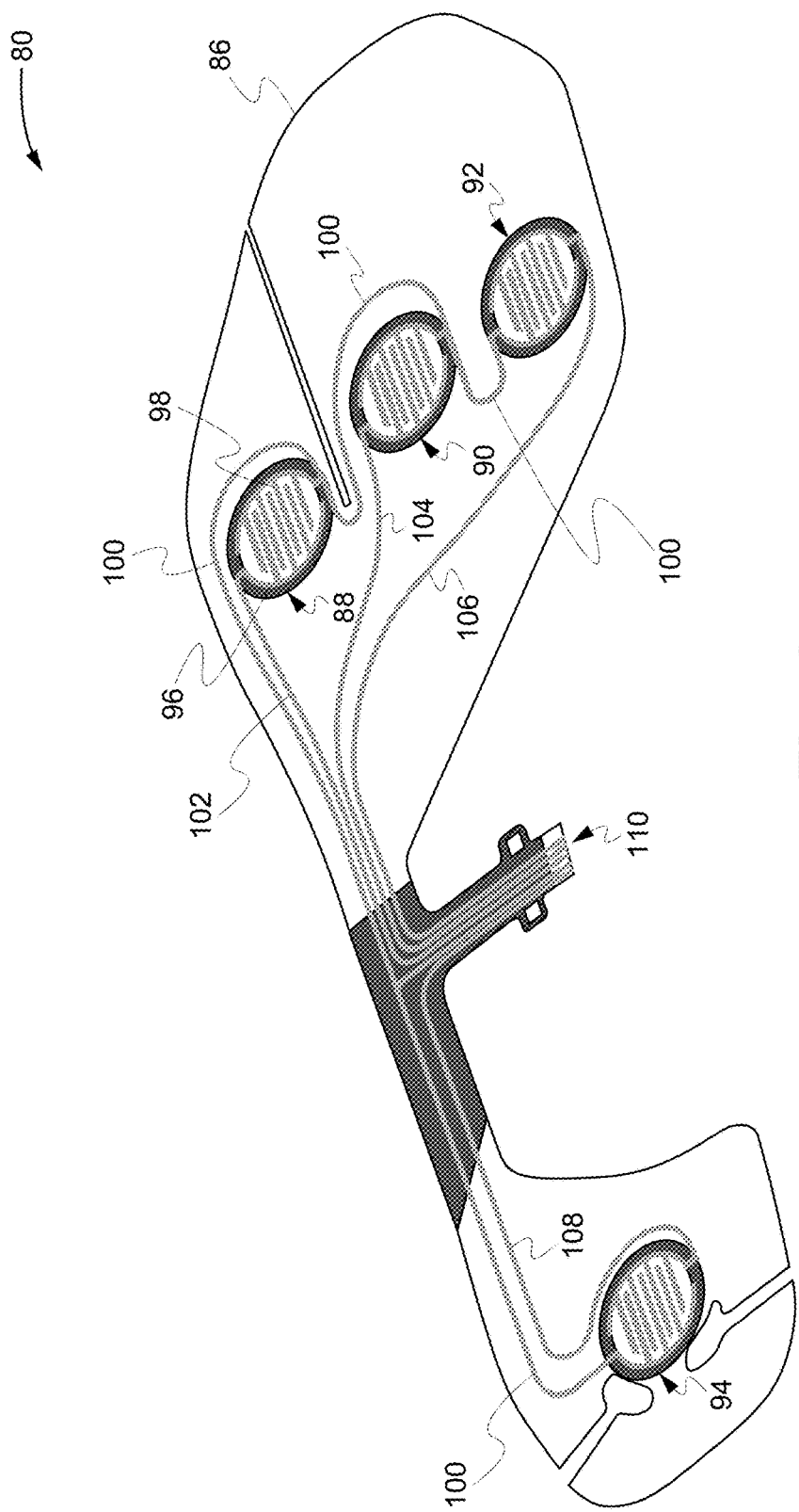
FIG. 9 illustrates the first layer of FIG. 8 according to some embodiments.

FIG. 9 illustrates the first layer 80 of FIG. 8 according to some embodiments. The FSR sensor and bladder system 78 is configured to have four sensor areas, shown as sensor areas 88, 90, 92, and 94 in FIG. 9. The first layer 80 includes a substrate 86 and patterned conductive traces and conductive traces corresponding to each of the four sensor areas. Specifically, patterned conductive traces 96 and 98 are positioned in the sensor are 88. The patterned conductive traces 96 and 98 are electrically isolated from each other and are therefore open circuited, similar to the patterned conductive traces 24 and 26 of the FSR sensor and bladder system 20. The patterned conductive trace 96 is connected to conductive trace 102, and the patterned conductive trace 98 is connected to conductive trace 100. Each of the other sensor areas 90, 92, 94 can have similar patterned conductive traces and conductive traces. One of the conductive traces, such as conductive trace 100, connected to a sensor area can be commonly connected to each of the other sensor areas as ground. The conductive traces 100, 102, 104, 106, 108 extend away from the corresponding sensing areas. Terminal ends 110 of the conductive traces 100, 102, 104, 106, 108 can be coupled to additional electronic circuitry (not shown) including, but not limited to, a current source and a current sensing circuit. The terminal ends of the conductive traces 100, 102, 104, 106, 108 can be coupled to connectors, such as staple connectors, or other conventional interconnection components for enabling connection to additional electronic circuitry that is off the FSR sensor and bladder system 78. In some embodiments, the terminal ends 110 are coupled to a flexible circuit board that in addition to the additional circuitry described above can also include signal processing circuitry, a microcontroller or the like, memory, wireless transmission circuitry, power circuitry, and the like.

Figure 10:
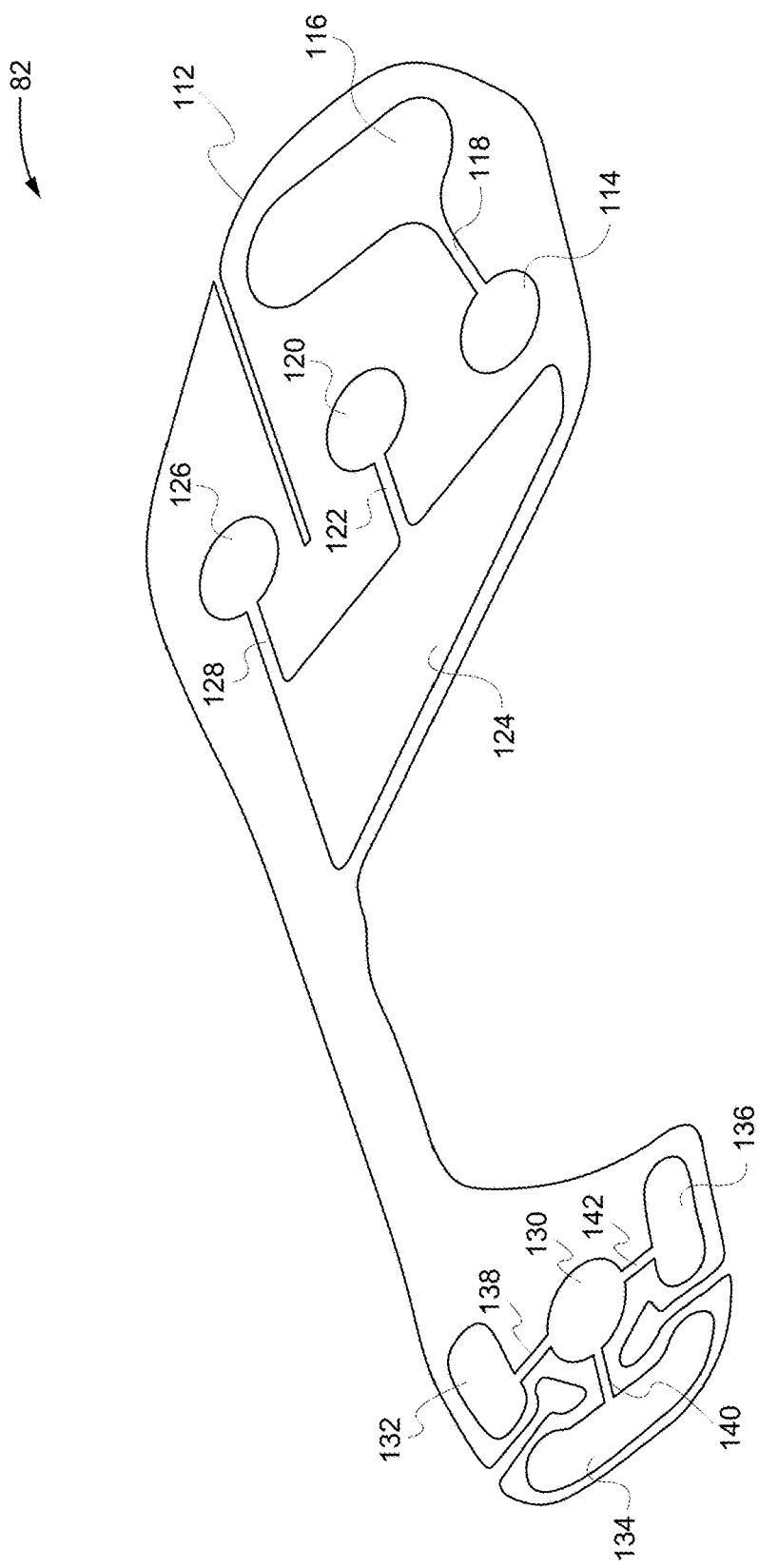
FIG. 10 illustrates the middle layer of FIG. 8 according to some embodiments.

FIG. 10 illustrates the middle layer 82 of FIG. 8 according to some embodiments. The middle layer 82 includes a substrate 112 having openings 114, 120, 126, and 130 that form the air cavities of corresponding sensor areas 92, 90, 88, 94, respectively. The substrate 112 also has openings 116, 124, 132, 134, and 136 that form bladder areas. In this exemplary configuration, air cavity 114 is connected to bladder area 116 by an air channel 118, air cavity 120 is connected to bladder area 124 by an air channel 122, air cavity 126 is connected to bladder area 124 by an air channel 128, and air cavity 130 is connected to bladder area 132 by an air channel 138, to bladder area 134 by an air channel 140, and to bladder area 136 by an air channel 142.

Figure 11:
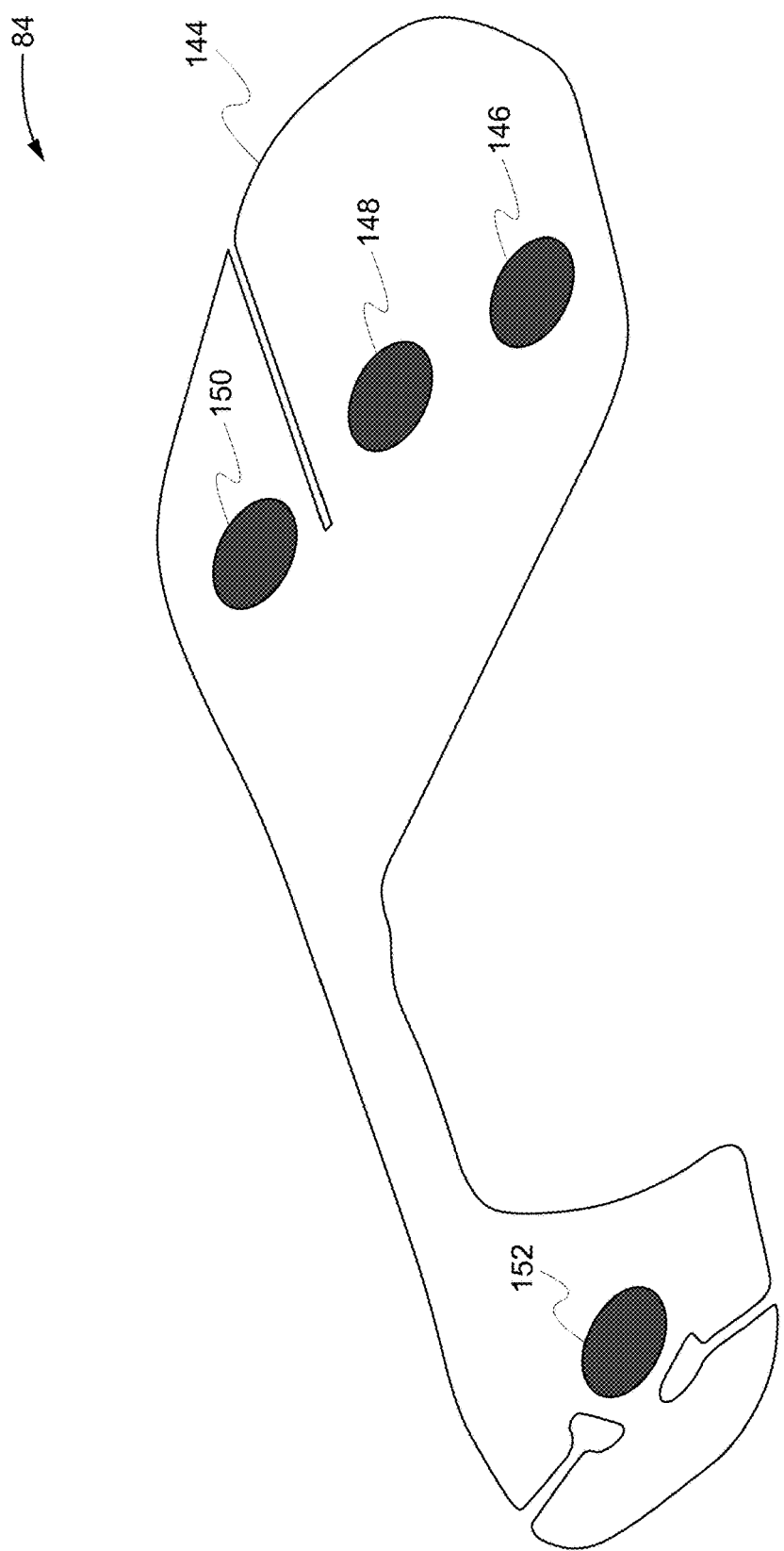
FIG. 11 illustrates the second layer of FIG. 8 according to some embodiments.

FIG. 11 illustrates the second layer 84 of FIG. 8 according to some embodiments. The second layer 84 includes a substrate 144 having conductive layers 146, 148, 150, and 152. The conductive layers 146, 148, 150, 152 can be each similar in form and function as the conductive layer 48 in FSR sensor and bladder system 20. The conductive layers 146, 148, 150, 152 correspond to sensor areas 92, 90, 88, 94, respectively.

The first layer 80, the middle layer 82, and the second layer 84 are stacked in a manner previously described. The FSR sensor and bladder system 78 can be configured with the bladders either filled with air or pre-collapsed in the static state.

The patterned conductive traces and conductive layers of the FSR sensor and bladder system 78 have a shunt mode configuration. It is understood that a similar FSR sensor and bladder system can be configured according to a thru mode configuration conceptually similar to the FSR sensor and bladder system 50 of FIGS. 5-7. It is understood that the number, orientation, and configuration of sensor areas, bladder areas, and other elements shown in FIGS. 9-11 is for exemplary purposes only and that the number, orientation, and configuration of the various elements of the FSR sensor and bladder system can be different than that shown.

The present application has been described in terms of specific embodiments incorporating details to facilitate the understanding of the principles of construction and operation of the FSR sensor with bladder system. Many of the components shown and described in the various figures can be interchanged to achieve the results necessary, and this description should be read to encompass such interchange as well. As such, references herein to specific embodiments and details thereof are not intended to limit the scope of the claims appended hereto. It will be apparent to those skilled in the art that modifications can be made to the embodiments chosen for illustration without departing from the spirit and scope of the application.

What is claimed is:

1. A force sensing resistor sensor comprising:
   a. a first layer comprising a first flexible substrate and a first conductive layer coupled to the first flexible substrate;
   b. a second layer comprising a second flexible substrate and a second conductive layer coupled to the second flexible substrate, wherein the first conductive layer and the second conductive layer form part of an electric circuit; and
   c. a middle layer comprising a middle substrate, a first opening through the middle substrate, and a second opening through the middle substrate, the first opening is interconnected to the second opening, wherein the first layer is stacked on the middle layer such that at least a portion of the first conductive layer is aligned over the first opening, further wherein the middle layer is stacked on the second layer such that at least a portion of the second conductive layer is aligned over the first opening, wherein the first layer covers the first opening and the second opening in the middle layer and the second flexible substrate covers the first opening and the second opening such that the first opening forms an air cavity and the second opening forms a bladder area interconnected to the air cavity, the air cavity and bladder area are a sealed environment.

2. The force sensing resistor sensor of claim 1 wherein the first layer is stacked on the middle layer such that the first conductive layer is facing the middle layer, and the middle layer is stacked on the second layer such that the second conductive layer is facing the middle layer.

3. The force sensing resistor sensor of claim 1 wherein the middle substrate further comprises an air channel, and the first opening is interconnected to the second opening through the air channel.

4. The force sensing resistor sensor of claim 1 wherein the portion of the first conductive layer aligned over the first opening, the first opening, and the portion of the second conductive layer aligned over the first opening form a sensor area.

5. The force sensing resistor sensor of claim 4 wherein the force sensing resistor sensor is configurable between a static state and an active state, wherein in the static state the portion of the first conductive layer in the sensor area is separated from the portion of the second conductive layer in the sensor area by air in the air cavity, further wherein in the active state at least one of the portion of the first conductive layer or the portion of the second conductive layer is forced into contact with the other of the first conductive layer or the portion of the second conductive layer.

6. The force sensing resistor sensor of claim 5 wherein forcing the portion of the first conductive layer and the portion of the second conductive layer into contact with each other forces air from the air cavity into the bladder area.

7. The force sensing resistor sensor of claim 6 wherein the force sensing resistor sensor is further configurable to return from the active state to the static state by removing the force applied to at least one of the portion of the first conductive layer or the portion of the second conductive layer, which separates the portion of the first conductive layer and the portion of the second conductive layer.

8. The force sensing resistor sensor of claim 7 wherein removing the force generates a vacuum in the air cavity that forces air from the bladder area back into the air cavity.

9. The force sensing resistor sensor of claim 5 wherein in the static state the bladder area is filled with air.

10. The force sensing resistor sensor of claim 5 wherein in the static state the bladder is pre-collapsed.

11. The force sensing resistor sensor of claim 5 wherein in the static state the electric circuit is open circuited, and in the active state the electric circuit is closed circuited.

12. The force sensing resistor sensor of claim 1 wherein the first conductive layer and the second conductive layer are configured according to a shunt mode configuration.

13. The force sensing resistor sensor of claim 1 wherein the first conductive layer and the second conductive layer are configured according to a thru mode configuration.

14. A method of making a force sensing resistor sensor, the method comprising:
   a. forming a first layer that includes forming a first conductive layer on a first substrate;
   b. forming a second layer that includes forming a second conductive layer on a second substrate;
   c. forming a middle layer that includes forming an air cavity and a bladder area within a third substrate, wherein the air cavity is coupled to the bladder area; and
   d. stacking the first layer, the middle layer, and the second layer with at least a portion of the first conductive layer facing the middle layer and aligned with the air cavity, and at least a portion of the second conductive layer facing the middle layer and aligned with the air cavity, wherein the portion of the first conductive layer, the portion of the second conductive layer, and the air cavity form a sensing area, further wherein the air cavity and the bladder area form a sealed environment within the force sensing resistor sensor.

15. The method of claim 14 wherein forming the middle layer further comprises forming an air channel in the third substrate, wherein the air channel connects the air cavity to the bladder area.

16. The method of claim 14 wherein the portion of the first conductive layer aligned over the first opening, the first opening, and the portion of the second conductive layer aligned over the first opening form a sensor area.

17. The method of claim 14 wherein the force sensing resistor sensor is configurable between a static state and an active state, wherein in the static state the portion of the first conductive layer in the sensor area is separated from the portion of the second conductive layer in the sensor area by air in the air cavity, further wherein in the active state at least one of the portion of the first conductive layer or the portion of the second conductive layer is forced into contact with the other of the first conductive layer or the portion of the second conductive layer.

18. The method of claim 17 wherein forcing the portion of the first conductive layer and the portion of the second conductive layer into contact with each other forces air from the air cavity into the bladder area.

19. The method of claim 18 wherein the force sensing resistor sensor is further configurable to return from the active state to the static state by removing the force applied to at least one of the portion of the first conductive layer or the portion of the second conductive layer which separates the portion of the first conductive layer and the portion of the second conductive layer.

20. The method of claim 19 wherein removing the force generates a vacuum in the air cavity that forces air from the bladder area back into the air cavity.

21. The method of claim 17 wherein in the static state the bladder area is filled with air.

22. The method of claim 17 wherein in the static state the bladder is pre-collapsed.

23. The method of claim 17 wherein in the static state the electric circuit is open circuited, and in the active state the electric circuit is closed circuited.

24. The method of claim 14 wherein the first conductive layer and the second conductive layer are formed according to a shunt mode configuration.

25. The method of claim 14 wherein the first conductive layer and the second conductive layer are formed according to a thru mode configuration.

\* \* \* \* \*